United States Patent
Ghosh et al.

(10) Patent No.: US 11,295,870 B2
(45) Date of Patent: Apr. 5, 2022

(54) MAGNETICALLY AUGMENTED PLASMONIC TWEEZERS

(71) Applicant: Indian Institute of Science, Bangalore (IN)

(72) Inventors: Souvik Ghosh, Bengaluru (IN); Ambarish Ghosh, Bengaluru (IN)

(73) Assignee: Indian Institute of Science, Bangalore (IN)

( * ) Notice: Subject to any disclaimer, the term of this patent is extended or adjusted under 35 U.S.C. 154(b) by 0 days.

(21) Appl. No.: 16/643,430

(22) PCT Filed: Sep. 3, 2018

(86) PCT No.: PCT/IN2018/050566
§ 371 (c)(1),
(2) Date: Feb. 28, 2020

(87) PCT Pub. No.: WO2019/043733
PCT Pub. Date: Mar. 7, 2019

(65) Prior Publication Data
US 2020/0258647 A1    Aug. 13, 2020

(30) Foreign Application Priority Data

Sep. 1, 2017   (IN) .............................. 201741031139

(51) Int. Cl.
*G21K 1/00* (2006.01)
*G02B 5/00* (2006.01)
(Continued)

(52) U.S. Cl.
CPC .............. *G21K 1/006* (2013.01); *G02B 5/008* (2013.01); *B82Y 15/00* (2013.01); *B82Y 20/00* (2013.01);
(Continued)

(58) Field of Classification Search
CPC .......... A61B 2017/00345; B82Y 15/00; B82Y 20/00; B82Y 25/00; B82Y 39/00;
(Continued)

(56) References Cited

U.S. PATENT DOCUMENTS 9,638,639 B2 *   5/2017  Fan ........................ B82Y 15/00
10,004,135 B2 *  6/2018  Ilic ........................... H05H 3/04
(Continued)

FOREIGN PATENT DOCUMENTS

WO   WO-2019043733 A1    3/2019

OTHER PUBLICATIONS

"International Application No. PCT/IN2018/050566, International Search Report and Written Opinion dated Feb. 11, 2018", (Feb. 11, 2018), 8 pgs.

(Continued)

*Primary Examiner* — Wyatt A Stoffa
(74) *Attorney, Agent, or Firm* — Schwegman Lundberg & Woessner, P.A.

(57) ABSTRACT

The present subject matter described herein relates to a Magnetically Augmented Plasmonic Tweezer (MAPT), a method for fabrication of the MAPT, and a method for trapping and maneuvering one or more colloidal particles inside a fluid. The fluid may correspond to a fluid inside a microfluidic device or a biological fluid. The MAPT can comprise a helical support structure to provide maneuverability in fluid. Further, a magnetic component is integrated in the MAPT for motion control. Plasmonic nanostructures are integrated in the MAPT for optical trapping of particles.

11 Claims, 14 Drawing Sheets

(51) Int. Cl.
*B82Y 15/00* (2011.01)
*B82Y 20/00* (2011.01)
*B82Y 25/00* (2011.01)
*B82Y 30/00* (2011.01)
*B82Y 35/00* (2011.01)
*B82Y 40/00* (2011.01)
*G01N 21/65* (2006.01)

(52) U.S. Cl.
CPC ............... *B82Y 25/00* (2013.01); *B82Y 30/00* (2013.01); *B82Y 35/00* (2013.01); *B82Y 40/00* (2013.01); *G01N 21/658* (2013.01)

(58) Field of Classification Search
CPC ...... B82Y 35/00; B82Y 40/00; G01N 21/658; G02B 5/008; G21K 1/006
See application file for complete search history.

(56) References Cited

U.S. PATENT DOCUMENTS

| | | | | |
|---|---|---|---|---|
| 10,330,600 | B2* | 6/2019 | Fan | G01N 21/658 |
| 10,722,250 | B2* | 7/2020 | Tasci | A61B 34/72 |
| 2002/0160195 | A1* | 10/2002 | Halas | B22F 1/02 |
| | | | | 428/403 |
| 2011/0124077 | A1 | 5/2011 | Sooryakumar et al. | |
| 2011/0270434 | A1* | 11/2011 | Fischer | B82Y 25/00 |
| | | | | 700/117 |
| 2012/0157346 | A1* | 6/2012 | Seul | C12Q 1/6837 |
| | | | | 506/13 |
| 2015/0380120 | A1 | 12/2015 | Wereley et al. | |
| 2016/0263391 | A1* | 9/2016 | Tasci | A61B 34/72 |
| 2016/0370316 | A1 | 12/2016 | Ndukaife et al. | |
| 2017/0115227 | A1* | 4/2017 | Fan | B82Y 15/00 |
| 2017/0370923 | A1* | 12/2017 | Gadegaard | G02B 1/002 |
| 2019/0178805 | A1* | 6/2019 | Su | G02B 6/1226 |

OTHER PUBLICATIONS

Huang, Jer-Shing, et al., "Origin and Future of Plasmonic Optical Tweezers", Nanomaterials 2015, 5(2), 1048-1065, (Jun. 12, 2015), 1048-1065.

"European Application Serial No. 18850510.1, Extended European Search Report dated Apr. 15, 2021", (Apr. 15, 2021), 7 pgs.

Ghosh, Ambarish, et al., "Controlled propulsion of artificial magnetic nanostructured propellers", Nano letters 9.6, (2009), pp. 2243-2245.

Huang, Jer-Shing, et al., "Origin and future of plasmonic optical tweezers", Nanomaterials 5.2, (2015), pp. 1048-1065.

* cited by examiner 100-1

100-2

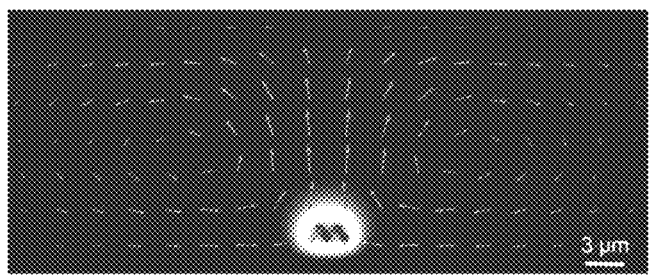
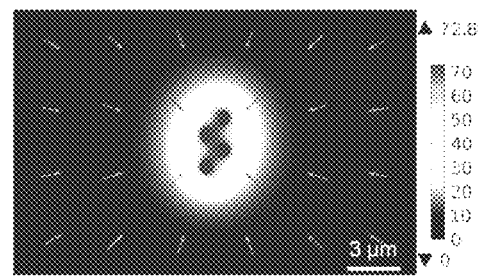
Fig. 5a              Fig. 5b

US 11,295,870 B2

MAGNETICALLY AUGMENTED PLASMONIC TWEEZERS

PRIORITY CLAIM TO RELATED APPLICATIONS

This application is a U.S. national stage filing under 35 U.S.C. § 371 from International Application No. PCT/IN2018/050566, filed on 3 Sep. 2018, and published as WO2019/043733 on 7 Mar. 2019, which claims the benefit under 35 U.S.C. 119 to India Application No. 201741031139, filed on 1 Sep. 2017, the benefit of priority of each of which is claimed herein, and which applications and publication are hereby incorporated herein by reference in their entirety.

TECHNICAL FIELD

The present subject matter relates, in general, to remotely controlling manipulation of particles in a fluidic media and, particularly to trapping and maneuvering sub-micrometer particles and nanoscale particles in a fluid.

BACKGROUND

Optical trapping and controlled manipulation have become an important area in biology and physics, and recently in commercial applications, useful for designing, manipulating, sorting, and assembling particles in a fluidic environment. While manipulation down to the level of atoms has been achieved on surfaces under high vacuum conditions, similar level of control is yet to be realized in fluidic media. This problem is essentially due to random collisions of the particles with the solvent molecules, which have strong randomizing effects as the particles become smaller. Conventional optical trapping uses forces exerted by an intense and tightly focused beam of light to trap and manipulate micro-particles. But the strength with which a particle can be trapped by an external force typically reduces with its volume, which becomes impractical as the size of the particle reduces to sub-micron dimensions. Because of the diffraction limit, light can only be focused down to about half the wavelength in the medium, thus setting a limit on maximum achievable optical gradient force from certain laser power level.

In this respect, plasmonic tweezers, which rely on localized electromagnetic fields near metallic nanostructures, offer an exciting alternative in generating strong trapping forces at low levels of optical illumination and have been used to trap particles as small as tens of nanometers.

In conventional plasmonic tweezers, a strong electromagnetic field is generated due to the resonant interaction (Localised Surface Plasmon Resonance) of the incident photons with free electrons in noble metals. This heavily confined electromagnetic field imparts an attractive optical gradient force to trap sub-micron and nanoscale particles. One can improve such trapping force by properly engineering the geometry of the metallic nanostructures. However, plasmonic resonance results in strong absorption of incident light that often leads to heating and even boiling (seen as bubbles) of the surrounding fluid. In general, such excessive heating is deleterious for trapping but can be useful for several thermoplasmonic applications including photothermal therapy, photothermal imaging, water desalination and many others.

Although plasmonic optical tweezers offer superior performance in reducing both the size of the trapped particle as well the required illumination intensity; there are certain disadvantages associated with this otherwise promising technique of optical manipulation. The region of enhanced electromagnetic field gradient around a plasmonic nanostructure is localized within a small region, typically a small fraction of wavelength of the incident light. Accordingly, trapping relies on the probability of a particle diffusing into a small volume, which is an inefficient process in the absence of additional forces. A modification with electrothermo plasmonic tweezers, as known in art, has circumvented this problem by generating a strong bulk fluid flow towards the plasmonic nanoantenna; but this technique has the additional requirement of having modulated electric fields in a medium with finite electrical conductivity, and therefore may not be applicable in many fluids. Also, one of the walls of the fluidic chamber needs to be patterned with nanoscale metallic features, which is a major disadvantage with such plasmonic tweezers, because the maximum distance over which a particle can be trapped and transported is limited by extent of the surface pattern. Another practical disadvantage with electrothermoplasmonic tweezer or any other plasmonic tweezer is that they lack the ability to select and transport desired particles from a mixture.

It is important to mention that the application of plasmonic tweezer is not only limited to trapping and manipulation, but this technique opens very important additional applications including Surface Enhanced Raman Scattering (SERS), Surface enhanced fluorescence (SEF) that relies on the enhanced light-matter interaction inside a plasmonic cavity. Another crucial application has been proposed that includes making a hybrid nanoscale assembly for testing next generation quantum technologies that requires selective manipulation of nanoscale constituents such as single quantum emitter (fluorescent nanodiamond, quantum dot etc.), carbon nanotube, metallic/semiconducting nanowire, etc. Hence the ability to rapidly select, transport, and assemble sub-micron and nanoscale particles will open up several possibilities for lab-on-chip applications. The applicability of this technique is not limited to ex vivo applications like lab-on-chip, but also applicable under in vivo conditions where nano and micron scale cargo are maneuvered inside an animal or human body. The cargo can be loaded with drugs which will thereby be useful for targeted drug delivery applications. However, a major obstacle towards achieving the use of plasmonic tweezers in various applications is diffusion-limited transport of the cargos to the plasmonic tweezers.

BRIEF DESCRIPTION OF DRAWINGS

The detailed description is explained with reference to the accompanying figures. In the figures, the left-most digit(s) of a reference number identifies the figure in which the reference number first appears. The same numbers are used throughout the drawings to reference like features and components.

FIG. 5a shows an out of plane view of convective velocity pattern and increased temperature distribution around MAPT-D1, in accordance with an embodiment of the present subject matter.

FIG. 5b shows an in-plane view of Convective velocity pattern and increased temperature distribution around MAPT-D1, in accordance with an embodiment of the present subject matter.

DETAILED DESCRIPTION

Figure 1:
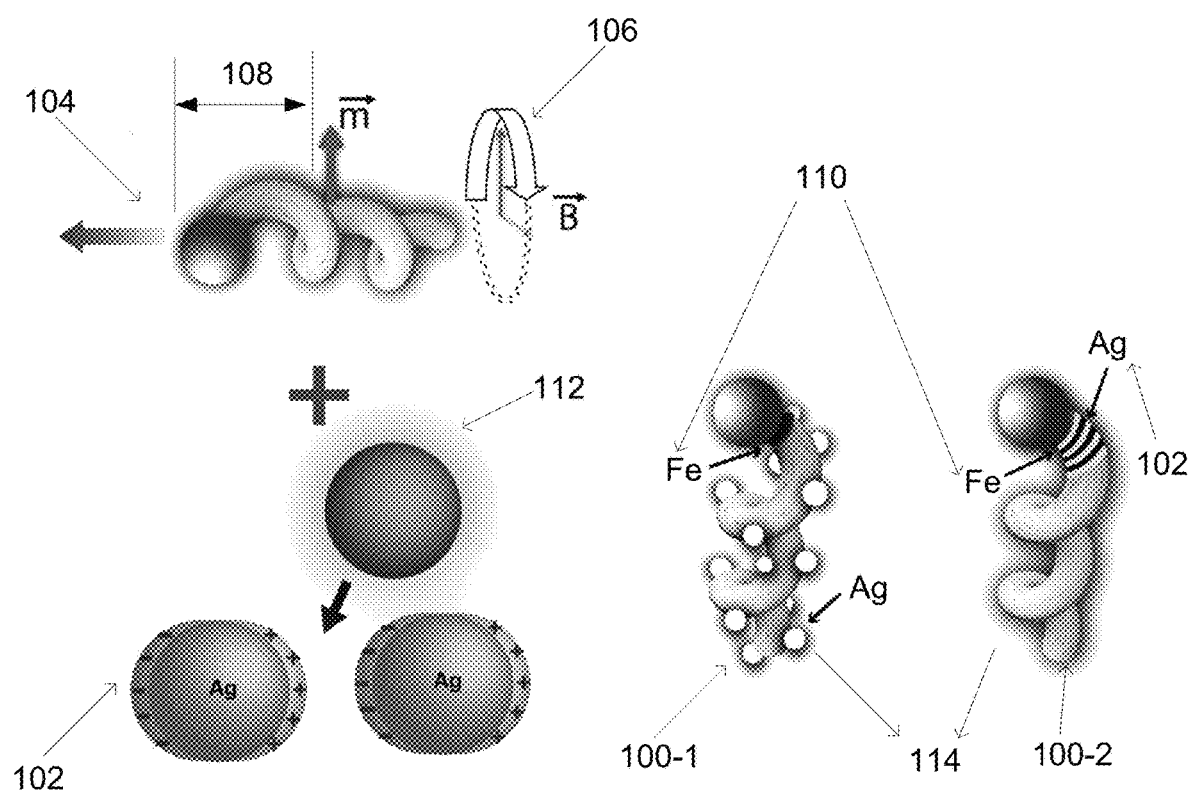
FIG. 1 illustrates an integration of plasmonic nanoparticles with Magnetically Augmented Plasmonic Tweezer (MAPT) that are structured as helical swimmers and designs of Plasmonic Tweezers (MAPT-D1 and MAPT-D2), in accordance with an embodiment of the present subject matter.

The present subject matter relates to techniques for developing artificial micro/nanomotors to capture, transport, release and position cargo in fluid media based on optical manipulation methodologies. The techniques can be used in lab-on-chip applications and also in vivo environment.

The main disadvantages of using typical plasmonic tweezers for optical manipulation are: (i) the process is slow since it relies on diffusion of particles to the small trapping volume as will be illustrated later in this description; (ii) requirement of a nano-patterned substrate to enable manipulation; and (iii) lack of selectivity and motion.

These problems are addressed in this disclosure and explained with examples. Various embodiments have been shown to overcome the slow diffusion limited speed by integrating plasmonic tweezers with magnetic nanoswimmers, thereby forming Magnetically Augmented Plasmonic Tweezer (MAPT). Embodiments of the present disclosure demonstrate dynamic transport of cargo at single and multiple particle level, and positioning and sorting of micro and nanoscale particles in a closed microfluidic chamber.

The methods described in this disclosure rely on integrating plasmonic properties to magnetically driven nanoswimmers, such as to develop the MAPT. The MAPTs can be actively steered to the particle of interest, subsequently be used to trap the particle(s), and finally to transport and release the cargo to a different location. The method can work in any microfluidic chamber and does not require nano-patterned surfaces to enable manipulation.

In an embodiment, the present subject matter describes techniques in developing artificial micro/nanomotors to capture, transport and release cargo in lab-on-chip applications that are based on optical manipulation methodologies. The particles trapped and released by the MAPTs are also referred to as cargo. The MAPTs, described herein, offer better performance than existing techniques in the following ways.

1) The method of cargo capture and release in most micromotors rely on chemical functionalization and/or having magnetic elements in both motor and the cargo, necessitating a high degree of specificity in their interaction. Plasmonic tweezers offer a more general solution and can work with almost any type of cargo.
2) The magnetic swimmers described here are powered externally and can therefore work remotely in any fluidic media. This class of swimmers have been shown to be non-toxic and can be moved in important biological fluids such as mucus, human blood, inside a living cell, in the peritoneal cavity of a living animal, in vitreous humor of the eye of a living animal etc.

3) Typically, vortex flow associated with magnetically actuated rods and doublets have been used to trap and transport colloidal cargo. This approach restricts the minimum size of the cargo till about half of the size of the magnetic carriers, and the smallest cargo manipulated was cylindrically shaped with dimensions 1 micrometer×2 micrometer. Also, the vortex flow works well in an unbounded fluid, which is not suitable for porous and constrained environments, such as most biological media. Due to thermal fluctuations, it is not possible to reduce the size of the magnetic carrier arbitrarily, which in turn limits how small a cargo can be trapped and transported using these mobile vortices. A similar limitation does not exist with the MAPTs described here. The trapping mechanism does not depend on the dimensions of the MAPTs thereby enabling a method to trap and maneuver particles that are about 30 times smaller than the carrier. By using different magnetic field configurations, it should be possible to maneuver multiple MAPTs autonomously, or along independent directions, which may have interesting microfluidic applications. For example, MAPTs may be used for massive, parallel manipulation of carbon nanotube which is one of the key constituent in hybrid nanoscale electronics. Quantum emitters such as Fluorescent nanodiamonds or quantum dots are also particles that need to be manipulated precisely for specific applications such as active quantum sensing, the realization of large area single photon sources etc.

4) The MAPTs can be mass produced and thereafter integrated seamlessly in standard lab-on chip systems, such as to carry out manipulation tasks that are beyond capabilities of currently used technologies.

Hereinafter, the terms 'magnetically augmented nanostructure', 'magnetically actuated nanostructure', 'magnetic micro-swimmers' and 'magnetic swimmers' may be used interchangeably. Further, the terms 'particle', 'cargo', 'cargo particle' and 'bead' may be used interchangeably.

In one embodiment, the present subject matter also relates to a system to fabricate magnetically actuated nanostructures/magnetic swimmers. In one example, plasmonic elements are integrated with magnetically actuated nanostructures to develop a MAPT. In one embodiment, the present subject matter relates to a system for manipulation of particles contained within a microfluid chamber or other fluid environment. For example, the system comprises an actuating mechanism to drive and transport the MAPT towards a particle at a first location in the fluid medium; and a source of light to illuminate the MAPT. The MAPT is configured to trap the particle upon illumination, transport the trapped particle from the first location to a second location on actuation by the driving mechanism, and release the trapped particle at the second location in the fluid medium. In an embodiment, to release or drop the trapped particle, the system is configured to reduce the illumination intensity of the source light below a threshold value, which depends on the size of the particle and the speed of the MAPT-particle system.

In an embodiment, the magnetic swimmers/the magnetically actuated nanostructures comprise a helical tail/support structure. The helical structure is provided with one or more plasmonically enhanced regions that are activated upon optical illumination. In one example, the helical tail/support structure may have a spherical head formed by a seed particle. Although the helical tail structure with the spherical head is described and illustrated herein, it is understood to a person skilled in the art that the magnetic swimmers may have a suitable profile that can be used to achieve controlled motion may be used. Further, these magnetic swimmers/helical swimmers are non-toxic and can be moved in biological fluids such as mucus, human blood and intracellular environment, as well as media inside a living animal In an embodiment, the MAPT is fabricated by an apparatus having a substrate holder, an evaporation system and a separation means. The substrate holder is configured to hold a substrate onto which seed particles are deposited to form a monolayer on the surface of the substrate. In one example, the seed particles are one of spherical silica particles or polystyrene particles. The seed particles may be deposited on the substrate using a Langmuir-Blodgett Trough.

With the present subject matter, it is possible to achieve magnetic manipulation in many different methods and those methods can be applied to the MAPTs. For example, it is possible to use a magnetic bead and use gradient of magnetic fields to pull the bead, in which case, the bead can be termed as a micro/nano-swimmer. Alternatively, it is possible to make a flexible structure containing magnetic elements which moves by a beating motion in the presence of oscillating field. Another possibility is to use magnetic rods that are rotated by magnetic fields, which achieve translation due to interactions with the nearby surfaces. The magnetic nanomanipulation technique that has been described herein is based on magnetic helical nanostructures which can be maneuvered by a rotating magnetic field, as shown in FIG. 1.

FIG. 1 illustrates an integration of plasmonic nanoparticles with magnetically actuated helical swimmers, in accordance with an embodiment of the present subject matter. As shown in the FIG. 1, the plasmonic nanoparticles 102, also referred to as plasmonic elements or plasmonic nanostructures, are integrated with magnetically actuated nanostructures/swimmers or helical swimmer structure 104 to obtain the MAPT.

As previously discussed, in an embodiment, the nanomanipulation technique used in the present subject matter is based on magnetic helical nanostructures which can be maneuvered by a rotating homogeneous magnetic field 106, as shown in schematic of FIG. 1 in a given direction. The motion may be similar to the way various microorganisms achieve translation by rotating helical flagella, which is a common method of maneuvering particles at small length scales (low Reynolds numbers).

The helical swimmer structure 104 comprises a helical support structure 114 to provide maneuverability in the fluid. A magnetic component is integrated in the helical support structure 114 to form the helical swimmer structure 104 which is used for motion control of the MAPT. In one example, the magnetic component comprises one or more of iron, cobalt, and nickel. In one example, the helical swimmer structure 104 of the MAPT shown in the FIG. 1 can be built by employing the Langmuir-Blodgett Trough process to deposit a seed layer on a substrate. The seed layer can be a monolayer of colloidal beads (for example, polystyrene beads) on the substrate. The magnetic component 110 is then deposited on the seed layer.

The plasmonic nanostructures 102 are also integrated in the helical support structure 114 for optical trapping of the colloidal particles. While the following description mentions the use of silica for preparing the helical support structure 114, it will be understood that other dielectric material, such as other oxides or fluorides, may be used alternatively or additionally to silica.

FIG. 1 illustrates two example variants MAPT-D1 100-1 and MAPT-D2 100-2 of a MAPT. In the fabrication of MAPT-D1, the plasmonic nanostructures 102 are integrated with the helical support structure 114 by depositing a plasmonic material on the helical support structure 114. The integration of the plasmonic nanostructures 102 by deposition of a plasmonic material on the helical support structure 114 comprises depositing a thin film of the plasmonic material on the helical support structure 114 and annealing the thin film to form the plasmonic nano-islands. In one example, the plasmonic material is made of one or more of Ag, Au, Cu, Al, TiN, and Aluminium-doped Zinc Oxide (AZO).

Initially, while keeping the substrate stationary, a layer of the plasmonic material is deposited, followed by the deposition of the magnetic component, then a layer of the plasmonic material. The thickness of the layer of the magnetic component is greater than and in the similar order of magnitude of a thickness of a layer of the plasmonic material. According to an example, 5 nm layer of Ag is deposited, followed by 60 nm of Fe, and another 5 nm layer of Ag. This was followed by growing a 3 µm film of SiO2 by rotating the substrate slowly at one revolution per hour per micrometer of deposited silica, resulting in the formation of a helical support structure 114. To enhance the plasmonic properties of the MAPT-D1, a thin film 5 nm of Ag is deposited on MAPT film, which is followed by annealing at 300° C. for 1 minute to dewet the film and form Ag nanostructures or nanoislands. This results in a maximum absorption wavelength of about 450 nm. Ag serves as an adhesion promoter between magnetic component and silica and also as a plasmonic nanoantenna to couple the incident light.

In the fabrication of MAPT-D2, the plasmonic nanostructures 102 are integrated with the helical support structure 114 by depositing the plasmonic material with the magnetic component 110. The integration of the plasmonic nanostructures 102 with the helical support structure 114 in this case is done by depositing alternate layers of the magnetic component 110 and the plasmonic material on the seed layer. In one example, the plasmonic material is made of one or more of Ag, Au, Cu, Al, TiN, and Aluminium-doped Zinc Oxide (AZO).

According to an example, 10 nm thick layer of Ag and 20 nm thick layer of Fe are deposited with three layers of Ag and two layers of Fe in between. This is followed by the growing the film of silica magnetic by rotating the substrate using Glancing Angle Deposition (GLAD), thereby resulting in formation of the helical support structure 114.

While the use of Fe is mentioned above as the magnetic component, it will be understood that other magnetic components may also be used. Once the MAPTs, such as MAPT-D1 or MAPT-D2, are formed, the substrate containing the MAPTs is sonicated in a suitable fluid, such as in deionized water, to obtain a suspension of MAPTs. In one example, the suitable fluid may be the same fluid in which the colloidal particles are present and need to be transported in. In another example, the suspension of MAPTs may be formed, for example, in deionized water and a small quantity of the suspension with the MAPT may be injected into the fluid, such as a biological fluid, such as the biological fluid is selected from blood, mucus, cellular fluid, fluid in an organ, and fluid in a tissue, or other fluid, where the colloidal particles to be transported are present. This may be done in vivo or in a lab-on-chip arrangement. Thus, the fluidic suspension containing both MAPTs and the colloidal particles is prepared.

As discussed above, FIG. 1 illustrates designs of Plasmonic Tweezers (MAPT-D1 and MAPT-D2), in accordance with an embodiment of the present subject matter. In the design of MAPT-D1, the magnetic component 110 is integrated to the helical support structure 114 to form the helical swimmer structure 104. The plasmonic nanostructures 102 are distributed throughout the surface of the helical swimmer structure 104. The plasmonic part or the plasmonic nanostructures 102 generate strongly localized electric field upon optical illumination, which impart attractive gradient force for trapping colloidal particles 112 of varying sizes.

In MAPT-D2, alternating layers of plasmonic nanostructures 102 and the magnetic component 110 are distributed on one end of the helical support structure.

In an embodiment, optical excitation of the plasmonic elements 102 results in strongly confined electromagnetic field gradient around the plasmonic elements 102 which generates an attractive gradient force on any nearby particle 112 (shown in FIG. 1). If the gradient force is large enough to overcome the Brownian fluctuation of the particle 112, it gets trapped. Thus, the captured particles are held by the plasmonic elements 102. One or more captured particles may be held around the surface of the helical support structure 114 as in MAPT-D1 or in a tiny portion in the vicinity of the spherical head as in MAPT-D2. Further, while FIG. 1 shows the particle 112 being trapped between two plasmonic nanostructures 10, in some case, the particle 112 may be attracted to and adhere to a single plasmonic structure 102.

As illustrated in the FIG. 1, the plasmonic nanostructures 102 can be distributed across surface of the helical support structure 114, or the plasmonic nanostructures can be provided towards one end of the helical support structure 114. The magnetic component 110 can be provided towards one end of the helical support structure 114. A small rotating magnetic field 106 may be used to turn the permanent magnetic moment of the magnetic MAPT synchronously with the field, resulting in a rotation and therefore translation (like a cork-screw) of the nano-helix in a fluid media. The direction of motion may be controlled in three dimensions by varying the plane and sense of the rotating field using a tri-axial Helmholtz coil built around a standard microfluidic device. The rotating magnetic field helps in maneuvering the MAPTs in the fluid media. The speed of the helix 108 was proportional to the frequency ($\Omega_B$) of the rotating magnetic field and the hydrodynamic pitch of the helix, provided the applied magnetic torque is greater than the viscous drag from the surrounding fluid. Accordingly, an oscillating magnetic field along with the DC field can be used to drive the MAPT.

In an aspect, the other techniques to drive the nano swimmer by using chemical fuels, electric field, magnetic gradient field, heat and even light may be used. Among all the techniques, rotating magnetic field is more efficient in pulling small particles with microscopic control at a noninvasive magnetic field (few tens of Gauss). In some applications, chemically powered motors can have an issue due to their lack of biocompatibility.

In one example, the helical structure is made of a material, such as silica or glass or other oxides or fluorides. To impart plasmonic properties, in the present subject matter, silver nanostructures are integrated with the helices, which results in a strong localization of electromagnetic field upon optical illumination. Although, the integration of the silver (Ag)

nanostructures with the helices is shown in the FIG. 1, it should be understood that other plasmonic materials such as Cu, Al, Au, TiN, AZO, etc. can also be used.

Figure 2A:
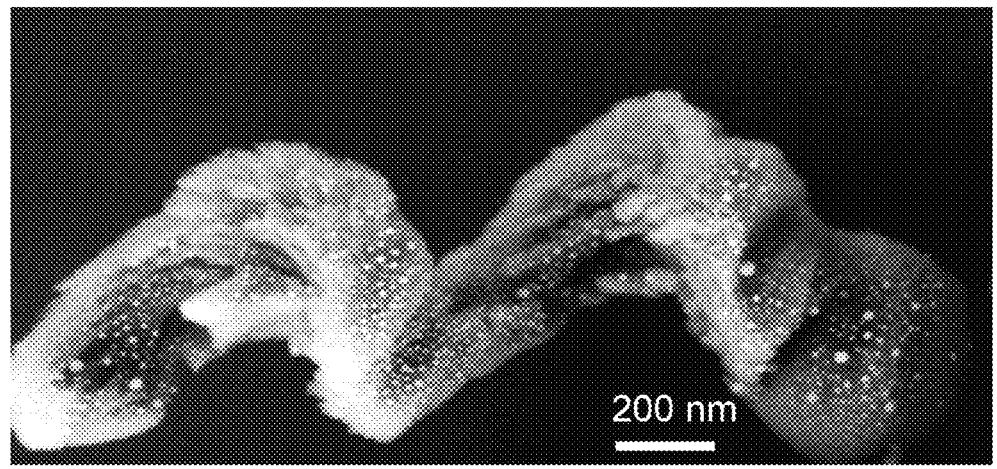
FIG. 2a shows a Scanning Electron Microscope (SEM) image of a MAPT-D1 with Ag islands across the body of the MAPT, in accordance with an exemplary embodiment of the present subject matter.
Figure 2B:
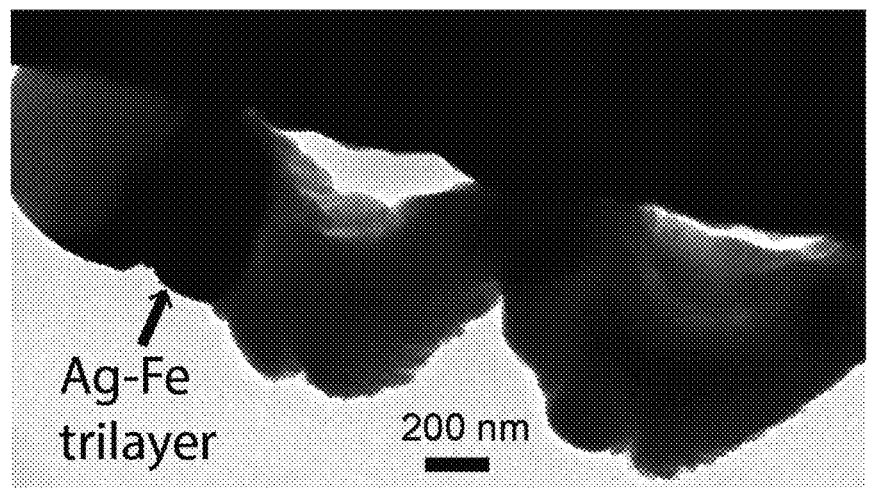
FIG. 2b shows a SEM image of a MAPT-D2 with three Ag layers at neck of helix, in accordance with an exemplary embodiment of the present subject matter

FIG. 2a shows a SEM image of a MAPT-D1 with Ag islands across the body of the MAPT, in accordance with an exemplary embodiment of the present subject matter. FIG. 2b shows a SEM image of a MAPT-D2 with plasmonic element at one end of helix, in accordance with an exemplary embodiment of the present subject matter. The key difference between the designs is in the way the plasmonic islands were integrated. For instance, the MAPT-D1 contains Ag islands, i.e., the plasmonic nanostructures 102, throughout the surface of the helical support structure 114 while the number of Ag elements was significantly lower in MAPT-D2. This results in more thermoplasmonic effects with MAPT-D1, which influence the trapping process. Although two designs of plasmonic tweezers are shown in the FIG. 1, it is possible to have many other designs with which plasmonic elements are integrated within the MAPT. For example, it may be possible to fabricate an optical resonator (e.g. bow-tie geometry) and then grow the magnetic helix over the resonator.

In an embodiment, different experiments are performed with different MAPT designs. The MAPTs are fabricated in large numbers with a yield greater than $10^8/cm^2$ of a suitable substrate (here, Si wafer). The manipulation experiments were carried out in standard microfluidic chambers of thickness around 20 µm, containing a suspension of colloidal particles and MAPTs.

In an embodiment, the methodology includes driving MAPTs close to the colloidal particle of interest, and this could be done either in the presence or absence of any illumination. Under sufficient optical power, the beads could get trapped by the MAPT, and subsequently the MAPT-bead system could be steered magnetically to the desired location. To drop the bead off, the illumination intensity was reduced below a threshold value, which depended on the size of the bead and the speed of the MAPT-bead system.

This approach circumvents two major disadvantages of optical manipulation with standard plasmonic tweezers; the MAPT could be driven towards the particle of interest rather than waiting for it to diffuse into the trap, and secondly, the optical manipulation could be carried out in standard microfluidic chambers that do not require specialized nanopatterned features.

Figure 3A:
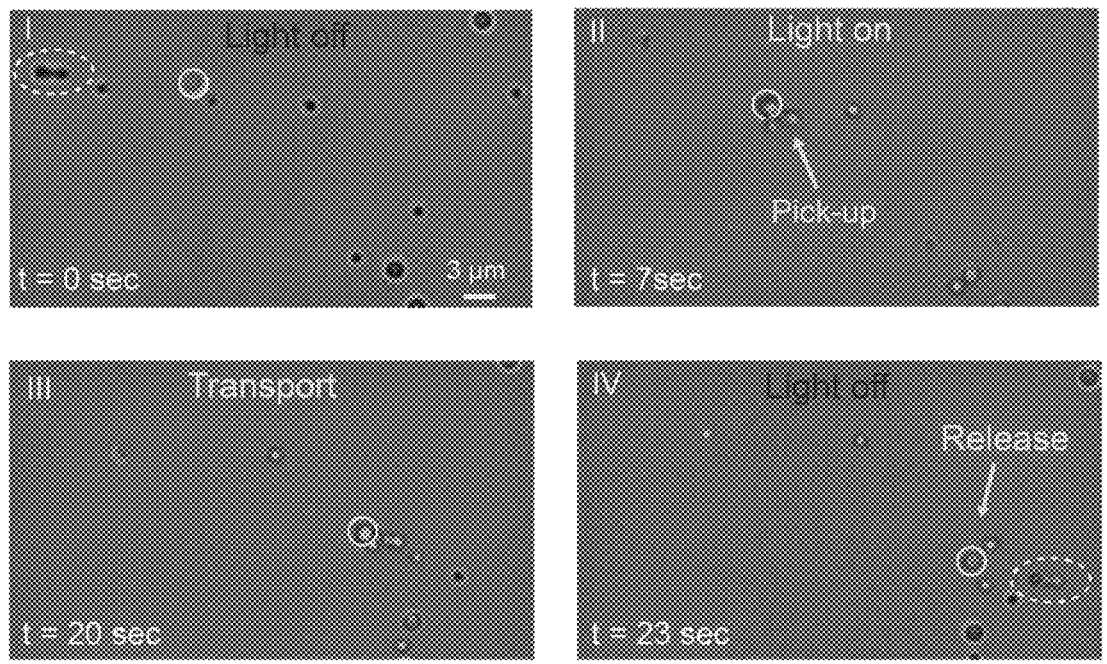
FIG. 3a illustrates demonstration of trapping, transporting and releasing of colloidal beads, in accordance with an exemplary embodiment of the present subject matter.
Figure 3B:
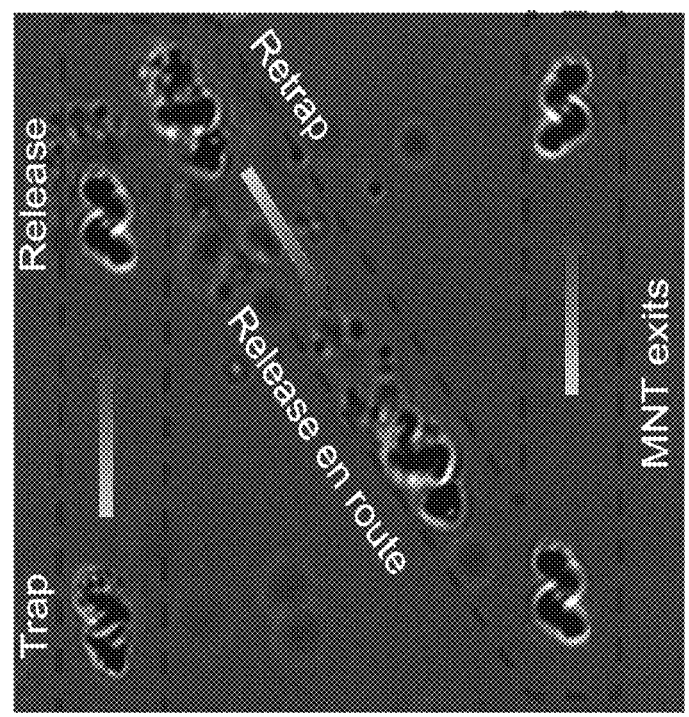
FIG. 3b illustrates manipulation of a collection of 500 nm silica beads at intensity of 30 kW/cm$^2$ to trace out the letter N, in accordance with an exemplary embodiment of the present subject matter.

FIG. 3a illustrates demonstration of trapping, transporting and releasing of colloidal beads, in accordance with an exemplary embodiment of the present subject matter. FIG. 3b illustrates manipulation of a collection of 500 nm silica beads at intensity of 30 kW/cm² to trace out the letter N, in accordance with an exemplary embodiment of the present subject matter.

The panel of images in the FIG. 3a shows the trapping, transportation and release of particles, for example, silica beads of two different sizes (1 µm and 2 µm). The frequency of the rotating field is set at 20 Hz, which resulted in the MAPTs moving at 2.7 µm/second. The MAPT reached close to the particles of interest in 6 seconds. In an embodiment, for illumination intensity of 18 kW/cm2, both beads are attached and the MAPT-bead system moved at V=1.8 µm/second. The beads were transported approximately 22 µm from their initial positions and subsequently released by simply lowering the optical intensity. Further, silica beads as small as 150 nm can be maneuvered at 0.7 m/second under illumination intensity of 30 kW/cm², as shown in the FIG. 3b. Although, in the present subject matter, the experiments were performed within the field of view of around 1000 µm², it is understood to a person skilled in the art that the present subject matter can maneuver the MAPTs and subsequently trap and release the cargo, anywhere across the entire microfluid device of size 2 cm*2 cm.

The FIG. 3b demonstrates the high level of spatio-temporal control over manipulation exercises achievable with the MAPTs. A collection of 500 nm silica beads were trapped by the MAPT and were transported and subsequently released in a different spot of the field of view. The beads were trapped again and then the MAPT was propelled to a different location with a reduced optical intensity and thereby releasing the trapped particles en route. Finally, the MAPT was driven away from the field of view, thereby completing a trajectory along the letter "N".

Figure 4A:
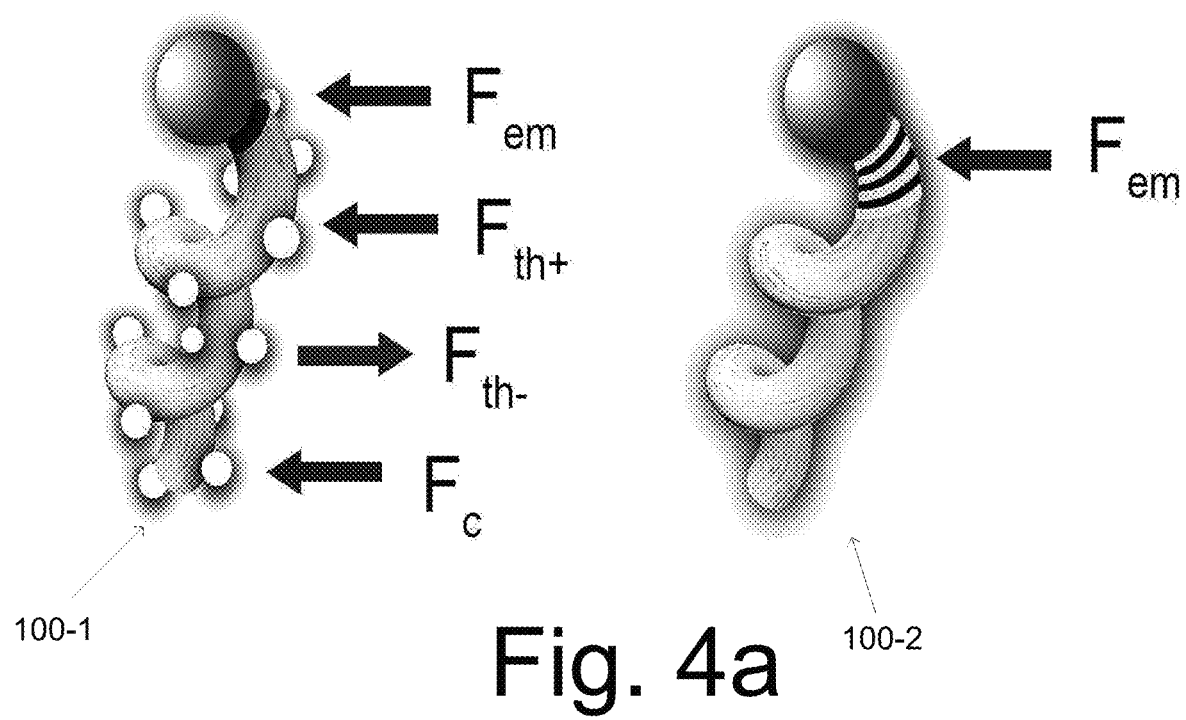
FIG. 4a shows a schematic of the different forces acting on MAPT-D1 and -D2, in accordance with an embodiment of the present subject matter.
Figure 4B:
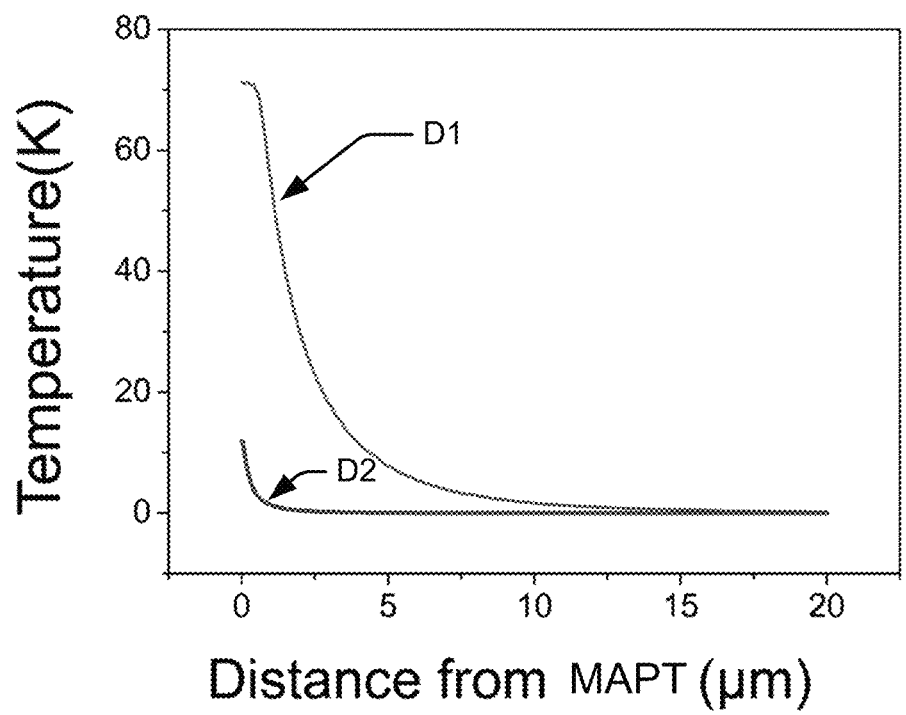
FIG. 4b is a graph showing variation of temperature as a function of distance from MAPT for the disclosed Plasmonic Tweezers (MAPT-D1 and MAPT-D2), in accordance with an embodiment of the present subject matter.
Figure 4C:
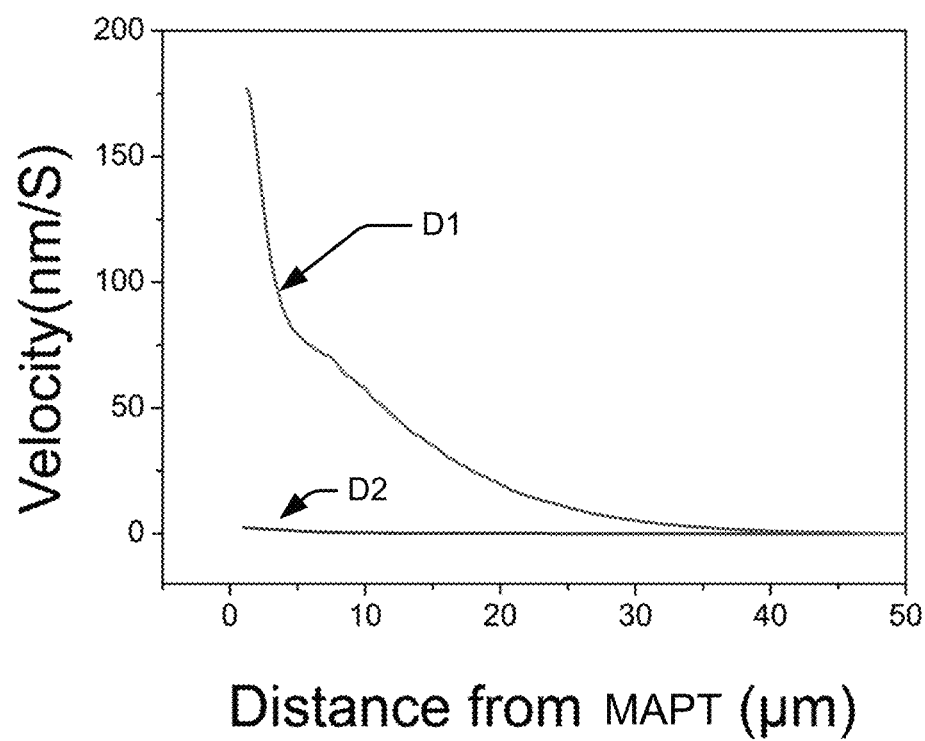
FIG. 4c is a graph showing convective flow velocity as function of distance from the MAPT for the disclosed Plasmonic Tweezers (MAPT-D1 and MAPT-D2), in accordance with an embodiment of the present subject matter.

In an embodiment, trapping mechanism and role of thermal effects in both the designs MAPT-D1 and MAPT-D2 is described herein with respect to FIG. 4a, FIG. 4b, and FIG. 4c.

FIG. 4a shows a schematic of the different forces acting on MAPT-D1 and MAPT-D2, in accordance with an embodiment of the present subject matter.

The absorption of light in the large number of Ag nanoislands across MAPT-D1 resulted in heat dissipated into the surrounding liquid, which gives rise to convective and more importantly thermophoretic forces close to the MAPT, where the thermal gradient (VT) was high. The direction of thermophoretic force depends on the sign of the Soret coefficient ($S_T$) of the trapped particle, and therefore could either aid or hinder the trapping process. The silica beads having negative $S_T$ were pushed onto the MAPT which increased with higher optical power.

The electromagnetic near field generates trapping forces ($F_{em}$) very close (<100 nm) to both the MAPT designs, while the thermopherotic ($F_{th}$) and convective ($F_c$) forces are only present with the design MAPT-D1. The magnitude of $F_{th}$ depends on the spatial gradient of temperature and appreciable within about few micro meters from the MAPT-D1 while the convective flow can range up to 100 µm. Therefore, the plasmonic nanostructures 102 of the MAPT-D1 and -D2 can interact with the surrounding colloidal particles by the thermophoretic force, near-field plasmonic force, or convective force.

FIG. 4b is a graph showing expected variation of temperature rise as a function of distance from MAPT for disclosed Plasmonic Tweezers (MAPT-D1 and MAPT-D2), in accordance with an embodiment of the present subject matter. FIG. 4c is a graph showing convective flow velocity as function of distance from the MAPT for disclosed Plasmonic Tweezers (MAPT-D1 and MAPT-D2), in accordance with an embodiment of the present subject matter.

In an embodiment, using numerical simulations, the variation of temperature as a function of distance from MAPT for disclosed Plasmonic Tweezers (MAPT-D1 and MAPT-D2), and the variation of the temperature with respect to the distance is shown in the FIG. 4b. Further, the convective flow velocity as function of distance from the MAPT is shown in the FIG. 4c. Further, the temperature rise is estimated (illustrated in FIG. 4b) using the numeric solutions and the resultant convective flow (illustrated in FIG. 4c) can be shown to be as high as 70° C. and 0.2 um/seconds respectively for MAPT-D1 for an intensity level 15 kW/cm². In case of MAPT-D2 temperature rise is just few degrees and therefore associated fluidic effects re negligible.

Further, the inward convective velocity pattern and temperature distribution around MAPT-D1 is shown in the FIG. 5a and the FIG. 5b. Under similar experimental conditions, the convective flow velocity is measured to be approximately 0.3-0.4 µm/seconds, which validates the overall numerical approach. In comparison, the number of plasmonic elements was far lesser and larger in size for MAPT-D2, which showed significantly weaker thermoplasmonic effects.

The relative performance of the two designs (MAPT-D1: Silica, and MAPT-D2: silica and PS) of various sizes is shown in FIG. 6a to FIG. 6d.

Figure 6A:
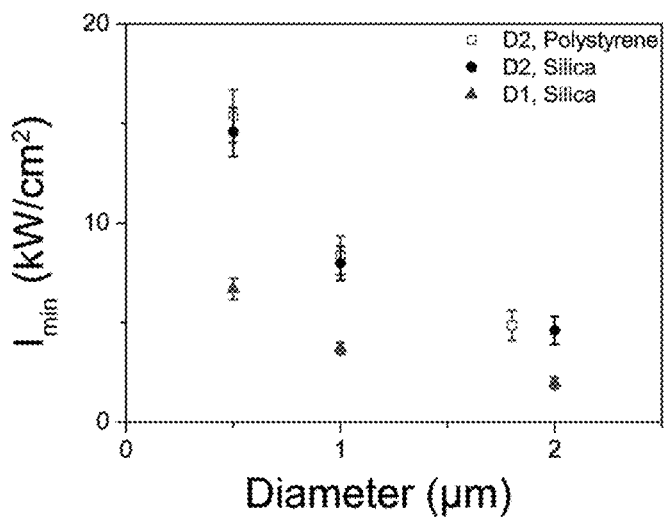
FIG. 6a is a graph showing variation of illumination intensity to trap a particle as a function of a size of the particle and material of the particle for designs MAPT-D1 and MAPT-D2, in accordance with an embodiment of the present subject matter.

FIG. 6a is a graph showing variation of illumination intensity to trap a particle as a function of a size and material of the particle for designs MAPT-D1 and MAPT-D2, in accordance with an embodiment of the present subject matter.

Upon illumination of an optical source, the MAPTs can trap the colloidal particles. As shown in the FIG. 6a, the minimum intensity ($I_{min}$) to trap a bead with a stationary MAPT reduced with increase in size. Due to efficient absorption of light of wavelength close to plasmon resonance wavelength, (here for example, wavelength of about 447 nm) heating is caused. Enhanced heating and corresponding thermophoretic attraction in design MAPT-D1 allowed silica beads to be trapped at slightly lower laser powers compared to design MAPT-D2. The magnitudes of $I_{min}$ for Silica and PS beads were almost the same, which proved that heating was indeed negligible for the design MAPT-D2.

Figure 6B:
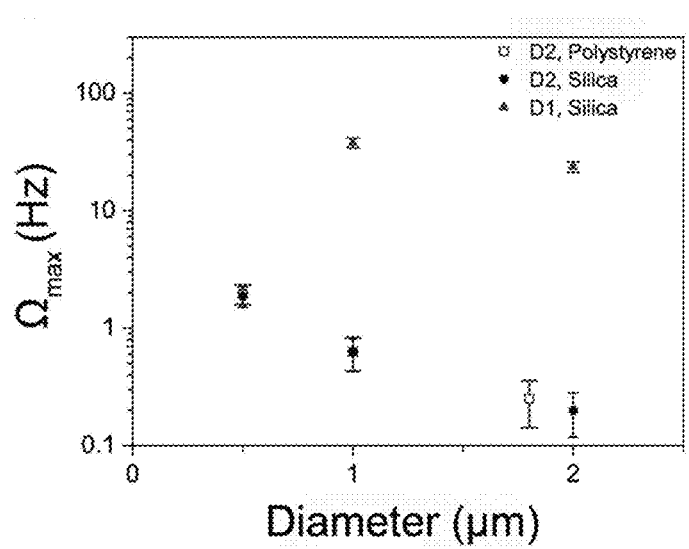
FIG. 6b is a graph showing variation of angular frequency as a function of a size of the particle for designs MAPT-D1 and MAPT-D2 for a fixed intensity of 22 kW/cm$^2$, in accordance with an embodiment of the present subject matter.

FIG. 6b is a graph showing variation of angular frequency as a function of a size of the particle for designs MAPT-D1 and MAPT-D2 for a fixed intensity of 22 kW/cm², in accordance with an embodiment of the present subject matter.

For trapping and maneuvering the colloidal particles, the MAPTs are driven to the colloidal particles by the rotating magnetic field. The maximum frequency ($\omega_{max}$) at which a MAPT-bead system can be rotated for a fixed illumination intensity of 22 kW/cm², is shown in the FIG. 6b. Experiments with MAPT-D1 showed larger $\omega_{max}$ implying greater speeds at which the MAPT-D1-bead system could be maneuvered.

Figure 6C:
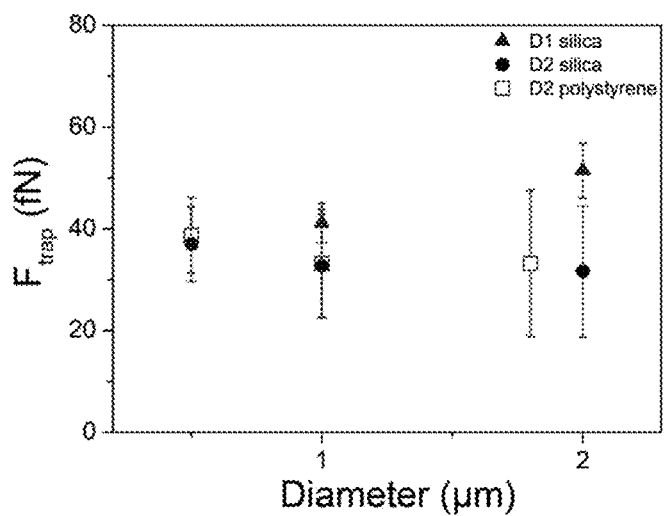
FIG. 6c is a graph showing variation of trapping force as a function of a size of the particle for designs MAPT-D1 and MAPT-D2 for a fixed intensity of 22 kW/cm$^2$, in accordance with an embodiment of the present subject matter.
Figure 6D:
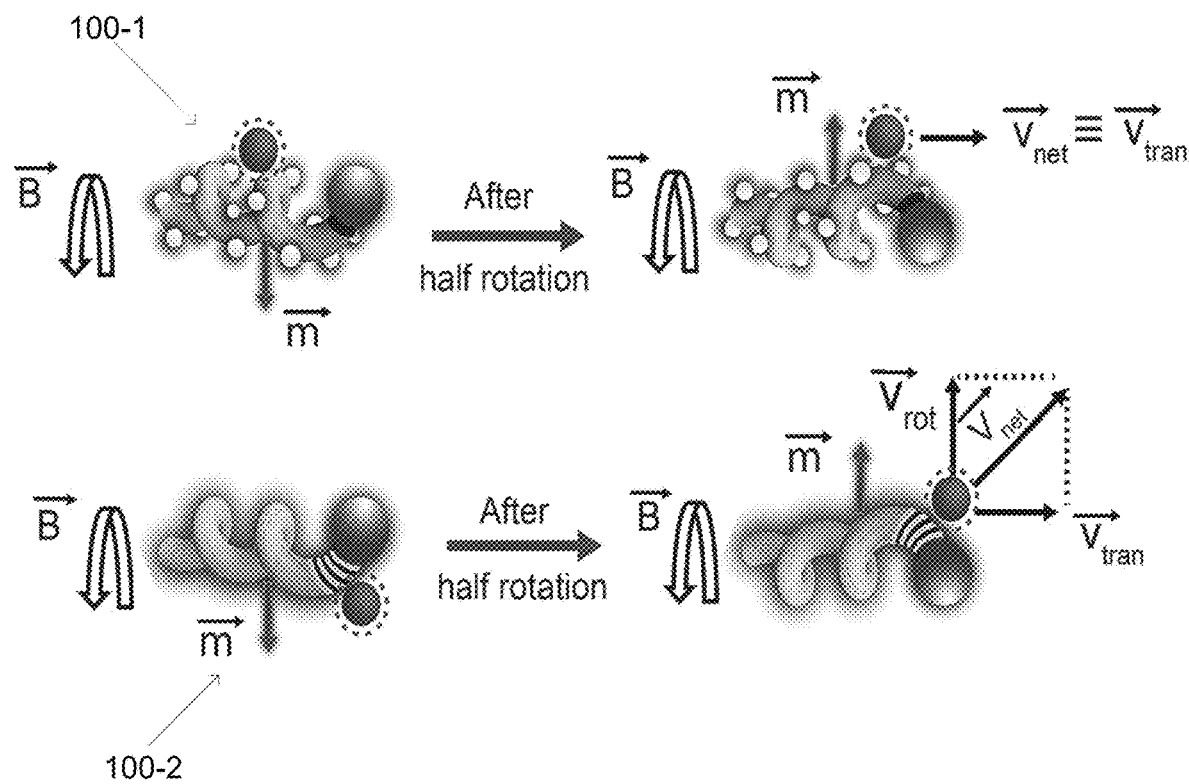
FIG. 6d shows different modes in which the MAPT-bead system moved and corresponding estimate of net velocity of the trapped particle, in accordance with an embodiment of the present subject matter.

The measurement of $\omega_{max}$ is used to estimate the net trapping force experienced by the beads, given by, $F_{trap}=6\pi R \eta \omega_{net}$ where R is the radius of the trapped bead and $\eta$ the viscosity of the surrounding medium respectively, and $\omega_{net}$ refers to the net speed of the beads at the maximum frequency $\omega_{max}$. The results of $F_{trap}$ for both designs are shown in FIG. 6c. For MAPT-D1, the beads did not rotate synchronously with the rotating helix, but were rather pushed against the MAPT surface, implying to be simply the translational speed of the MAPT-bead system (see FIG. 6d). This is different in MAPT-D2, where the beads rotated along with the MAPT and therefore also had contributions from the rotational motion around the helix axis. The trapping force for MAPT-D2 was primarily due to electromagnetic near field gradients and was independent of size of the beads. On the other hand, the trapping force for MAPT-D1 mostly originated through thermoplasmonic forces which increased for larger beads (larger $S_T$). To summarize this discussion, MAPT-D1 was preferable for materials with positive $S_T$ and offered higher manipulation speeds. On the other hand, the solution offered by MAPT-D2 was applicable to colloidal particles of any $S_T$, although with reduced propulsion speeds. Note it was possible to trap colloids between 120 nm and 1.8 µm at illumination intensities 5-50 kW/cm² with design MAPT-D2, which corresponds to comparable or even better efficiency than state-of-the art plasmonic tweezers.

Figure 7A:
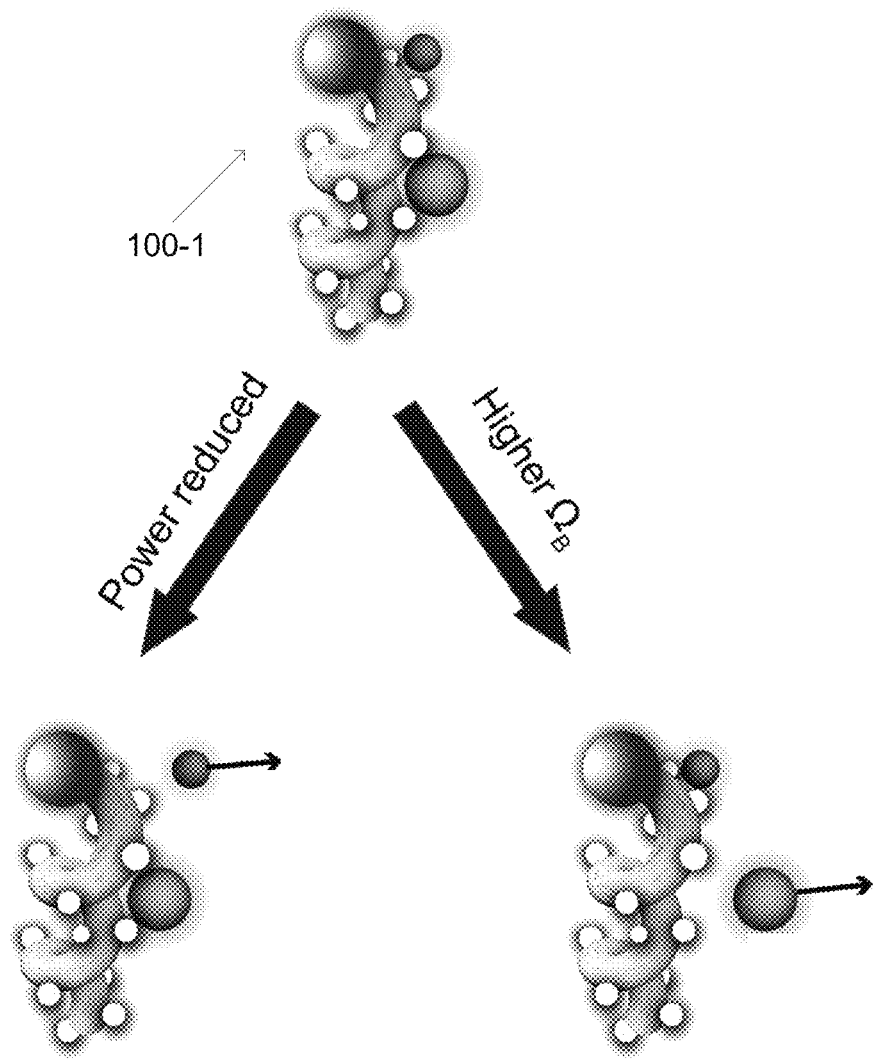
FIG. 7a illustrates schematic of two ways to transport beads selected by size, in accordance with an embodiment of the present subject matter.
Figure 7B:
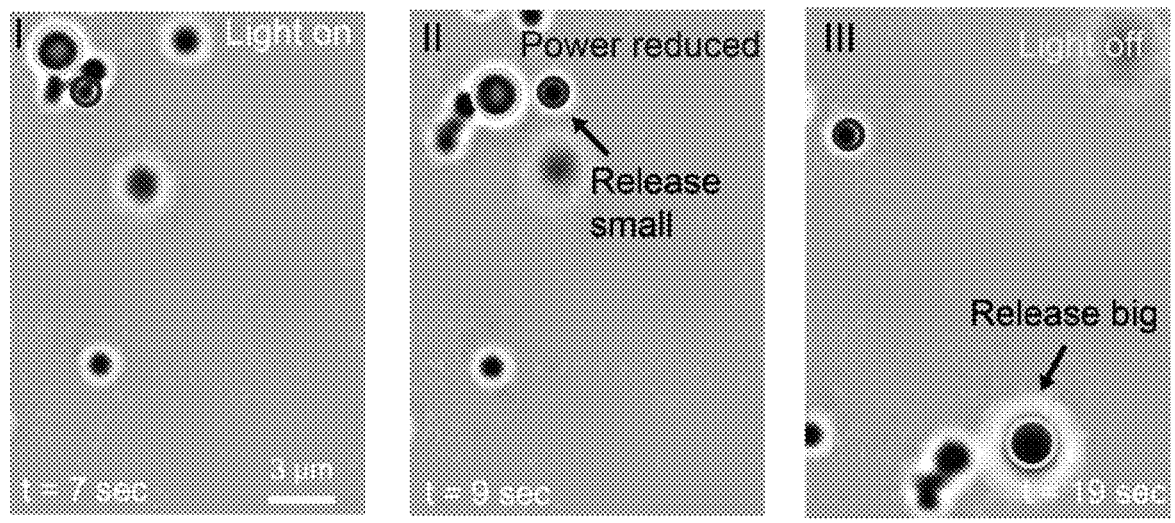
FIG. 7b illustrates a transporting of a 2 μm silica bead using optical intensity 12 kW/cm$^2$, in accordance with an embodiment of the present subject matter.
Figure 7C:
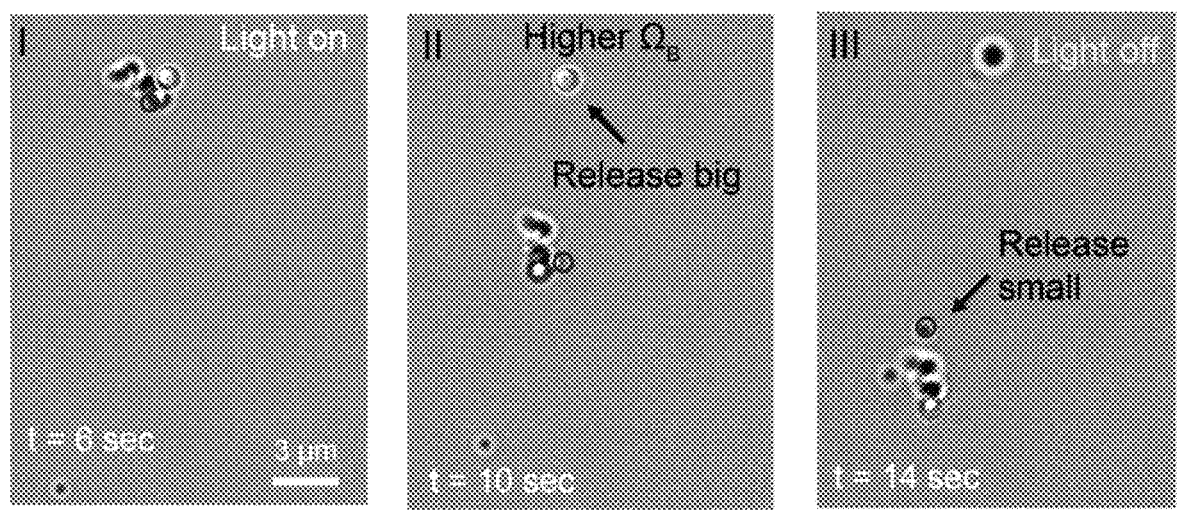
FIG. 7c illustrates a transporting of a 500 nm PS bead and releasing 1 μm silica by maneuvering the MAPT at 1 Hz, in accordance with an embodiment of the present subject matter

In the FIG. 7a to FIG. 7c, size selective transport by MAPT is described. This may be useful in varieties of microfluidic applications such as sorting. This is a unique capability of the MAPTs that does not exist with plasmonic tweezers or micro-swimmers individually but have been made possible due to the confluence of two independent manipulation techniques. The selective trapping of the colloidal particles based on size, is done by tuning the illumination intensity of the optical source or by tuning the rotation frequency of the MAPT. FIG. 7a illustrates schematic of two ways to transport beads selected by size, in accordance with an embodiment of the present subject matter. FIG. 7b illustrates a transporting of a 2 µm silica bead and releasing 1 µm silica bead using optical intensity 12 kW/cm², in accordance with an embodiment of the present subject matter. FIG. 7c illustrates a transporting of a 500 nm PS bead and releasing 1 µm PS bead by maneuvering the MAPT at 1 Hz, in accordance with an embodiment of the present subject matter.

FIG. 7a, FIG. 7b and FIG. 7c demonstrates size selective transport by MAPTs that can be useful in microfluidic applications, such as sorting. FIG. 7a, FIG. 7b and FIG. 7c is explained for design MAPT-D1. However, it is understood to a person skilled in the art that any suitable MAPT developed by integrating plasmonic tweezers with magnetic nanoswimmers can be used in microfluidic applications.

FIG. 7a shows a novel-size based sorting scheme. Two beads of unequal sizes are trapped on the MAPT-D1. The smaller bead may be released by reducing the illumination intensity, and thereby selectively transport the larger bead, as shown in the FIG. 7b. Alternatively, by choosing by an appropriate rotation frequency, it is possible to release the larger bead, because it experiences higher drag and therefore ejected at a lower speed. This is in accordance with the size dependence of $\omega_{max}$, as shown in the FIG. 6b. The smaller bead can therefore be carried to a different location, as shown in the FIG. 7c.

The experiments are carried out with a wide variety of colloidal materials using MAPTs, beyond standard silica and PS beads.

Figure 8A:
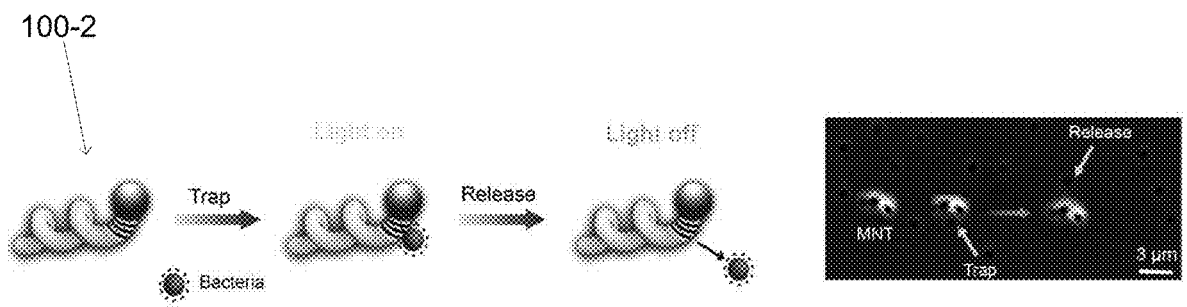
FIG. 8a shows a process of trapping and releasing biological materials, here bacteria (*Staphylococcus aureus*) under illumination 30 kW/cm$^2$, in accordance with an embodiment of the present subject matter.
Figure 8B:
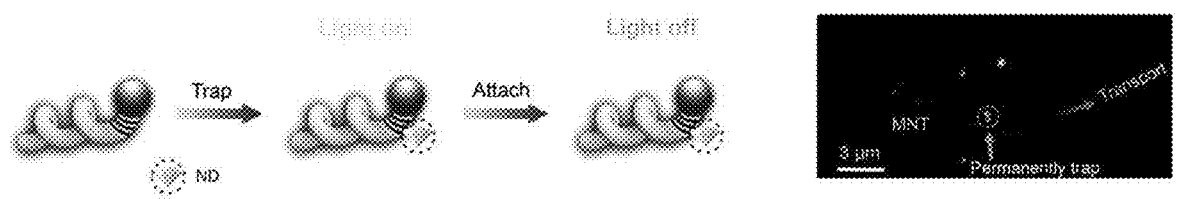
FIG. 8b shows a process of permanent trapping of fluorescent nano diamonds to the MAPT using optical illumination 50 kW/cm$^2$, in accordance with an embodiment of the present subject matter.

FIG. 8a shows a process of trapping and releasing biological materials, here bacteria (*Staphylococcus aureus*) under illumination 30 kW/cm², in accordance with an embodiment of the present subject matter. FIG. 8b shows a process of permanent trapping of fluorescent nanodiamonds to the MAPT-D2 using optical illumination 50 kW/cm², in accordance with an embodiment of the present subject matter. Fluorescent nanodiamonds after required chemical functionalization can be permanently attached to the MAPTs. FIG. 8a and FIG. 8b is explained for design MAPT-D2. However, it is understood to a person skilled in the art that any suitable MAPT developed by integrating plasmonic tweezers with magnetic nanoswimmers can be used.

As shown in the FIG. 8a, a biological material, here sub-micron size *Staphylococcus aureus* bacteria may be trapped and transported under illumination 30 kW/cm², and subsequently released by turning the illumination off. This shows that the MAPT-D2 can be used for bio-manipulation not only at reduced optical intensities but with faster speed which may find potential application in biological cargo manipulation such as cell sorting.

In certain cases, by choosing materials with appropriate surface properties, it may be possible to attach the colloidal cargo permanently. A particularly attractive example is of fluorescent nanodiamonds, which are promising candidates for cutting-edge biomedical and electronic applications. The unique spin and optical properties of nitrogen-vacancy (NV) centres in nanodiamond (ND) have attracted wide interest in diverse research fields, ranging from quantum optics, nanoscale magnetometry to biomedical imaging and tracking. To take full advantage of the highly sensitive applications of diamond-NV centres that rely on tuneable, bright and photo-stable fluorescence, it is required to bring the ND close to the position of interest and do the measurement. But so far, the measurements were taken only in a passive manner as NDs show strong Brownian fluctuation in fluid due to their nano size. In the present subject matter, a technique using the MAPTs to transport single as well as multiple NDs anywhere inside a fluidic volume with great control, is described.

As shown FIG. 8b, the carboxyl-functionalized nanodiamonds (average diameter 120 nm, Sigma Aldrich), who are known to have affinity to noble metal were optically trapped by the MAPT-D2 and thereafter were permanently attached to the MAPT-D2 surface using optical illumination 50 kW/cm$^2$. Once attached, the MAPT-nanodiamond system was maneuvered in 3D with or without the trapping illumination. The active 'ND-MAPT' can be steered to any desired location inside a fluidic chamber to perform several sensing measurements. This may be particularly important for probing the local environment of a biological specimen. As we show later, the technique disclosed in the present subject matter permits accurate positioning of MAPT-cargo at specific locations on a substrate, which will be very useful in realizing many other applications envisioned with fluorescent nanodiamonds. FIG. 8a and FIG. 8b is explained for design MAPT-D2. However, it is understood to a person skilled in the art that any suitable MAPT developed by integrating plasmonic tweezers with magnetic nanoswimmers can be used.

FIG. 9a to FIG. 9f describes schemes of nanoscale assembly. In particular, FIG. 9a to FIG. 9f describes two schemes to demonstrate how the MAPTs can be used for nanoscale assembly, and how they offer greater speed and versatility compared to existing techniques. In an embodiment, the MAPT described in FIG. 9a to FIG. 9f is MAPT-D1. In another embodiment, the MAPT described in FIG. 9a to FIG. 9f is MAPT-D2. Yet in another embodiment, the MAPT described in FIG. 9a to FIG. 9f is any MAPT developed by integrating plasmonic tweezers with magnetic nanoswimmers.

Figure 9A:
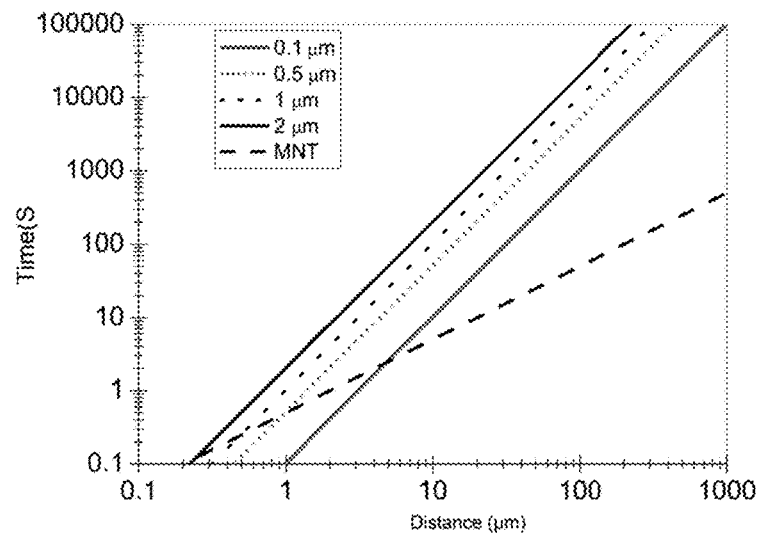
FIG. 9a shows time taken by MAPT for bringing cargo to a trap (dotted lines) over passive diffusion (solid lines for various cargo sizes) from a certain distance, in accordance with an embodiment of the present subject matter.

In the first scheme shown in FIG. 9a, the passive diffusion of a colloidal cargo into a trap, e.g. an optical trap, is compared with the case where the cargo is actively loaded into the trap by the MAPT.

Assuming the initial distance of the cargo from the trap to be L, the improvement in loading time is vL/D, where v is the speed of the MAPT and D is the diffusion constant of the cargo.

Figures 9B, 9C:
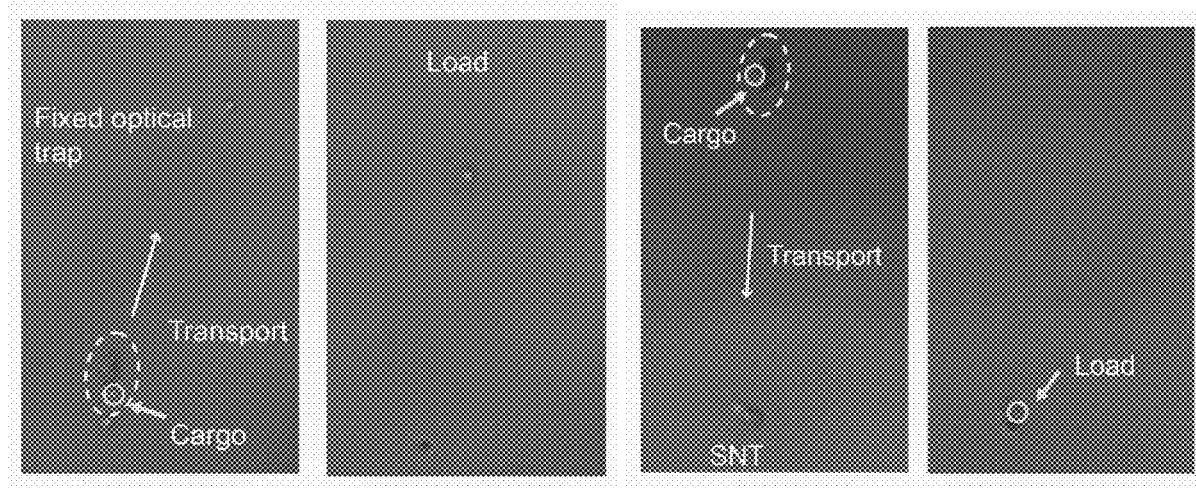
FIG. 9b and FIG. 9c shows demonstration of MAPT loading a conventional optical trap and plasmonic trap, in accordance with an embodiment of the present subject matter.

In an embodiment, a demonstration with an optical trap and two colloidal particles located about 50 μm away from the trap is shown in FIG. 9b. The MAPT is selectively carried one of the particles, and subsequently loads the trap, while the other particle remained at approximately the same position. The total time taken was 40 seconds, which demonstrates an improvement of 130 in comparison to passive diffusion.

A particularly attractive demonstration is shown in FIG. 9c, where the MAPT is shown to load a plasmonic trap, here an optically printed MAPT on a substrate. The standard plasmonic tweezers are speed-limited by the slow random diffusion of cargo. Existing techniques to improve speed of standard plasmonic tweezers either require invasive optical fibers with limited range of motion (<15 μm) or necessitate the application of modulated electric field within a customized microfluidic chamber. The solution provided by the present subject matter speeds up the trapping process dramatically without compromising the generality with which plasmonic tweezers can be applied to a wide variety of materials and in a variety of fluids.

Figure 9D:
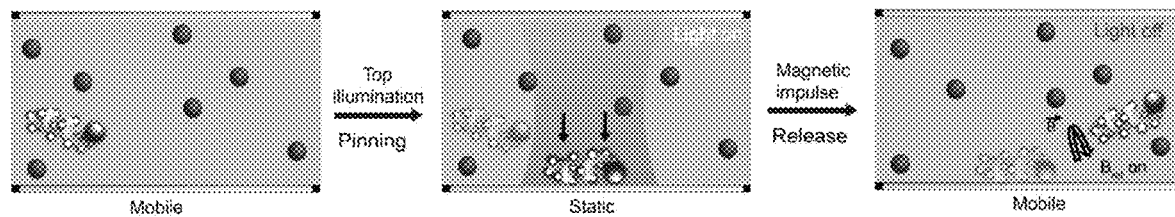
FIG. 9d shows a schematic of optomechanically controlled positioning of the MAPT, in accordance with an embodiment of the present subject matter.
Figure 9E:
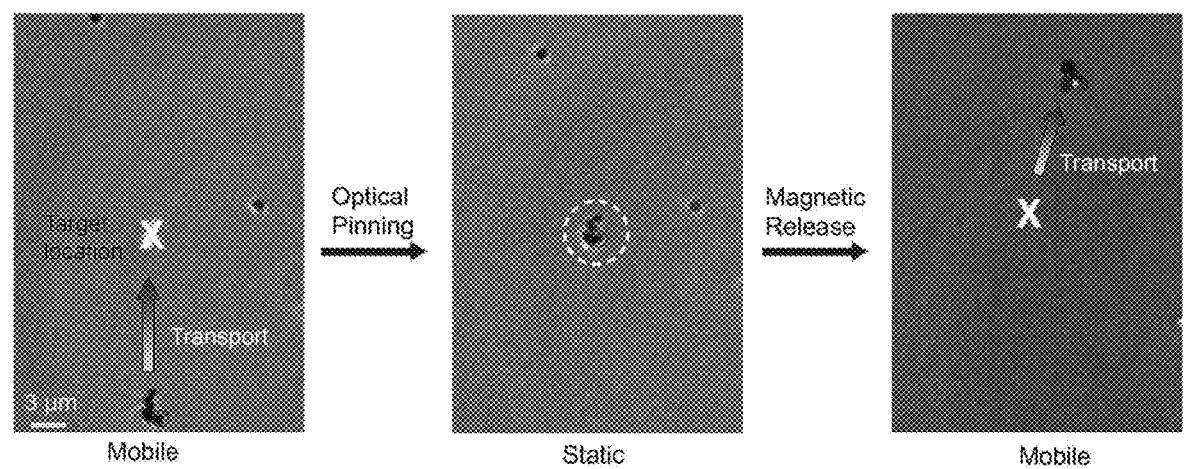
FIG. 9e shows a demonstration of static and dynamic nano tweezing, with pinning-depinning of the MAPT on the chamber surface controlled by radiation pressure and magnetic fields, in accordance with an embodiment of the present subject matter.

An alternate second scheme of accurate positioning of nano-particles, demonstrating the versatility of MAPTs is shown in FIG. 9d, where a mobile nano tweezer can be made static, by optically pushing and therefore "printing" it onto the substrate. This is accomplished by an additional illumination from top of the chamber with intensity 110 kW/cm$^2$, where the strong radiation pressure pushes and binds the MAPT onto the substrate. The MAPTs may be released from the substrate, by reducing the optical power and momentarily applying a high magnetic field (~200 G) in slow (~Hz) rotating configuration. By pinning and unpinning the MAPT using optical and magnetic fields, we could convert any spot on the chamber as a plasmonic tweezer, without requiring any prior nanopatterning. Crucially, the pinning-unpinning manipulations could be carried out even with the cargo trapped on the MAPT, as shown in FIG. 9e.

The techniques described in FIG. 9a to FIG. 9e automatically suggest a large number of possibilities, where colloids, e.g. nanodiamonds with nitrogen vacancies can be picked up from a certain location on the substrate or from a region in the fluidic chamber by a MAPT. Subsequently, the MAPT can bring the nanodiamond to a certain location. At this point, the diamond can be released and placed at a location or maybe the MAPT-diamond combination can be optically printed on the substrate. This can be followed by analysis and measurements involving electrical, optical and/or magnetic fields, as deemed useful for the particular application. The entire process can be parallelized suing many MAPTs, and repeated multiple times, if necessary.

Figure 9F:
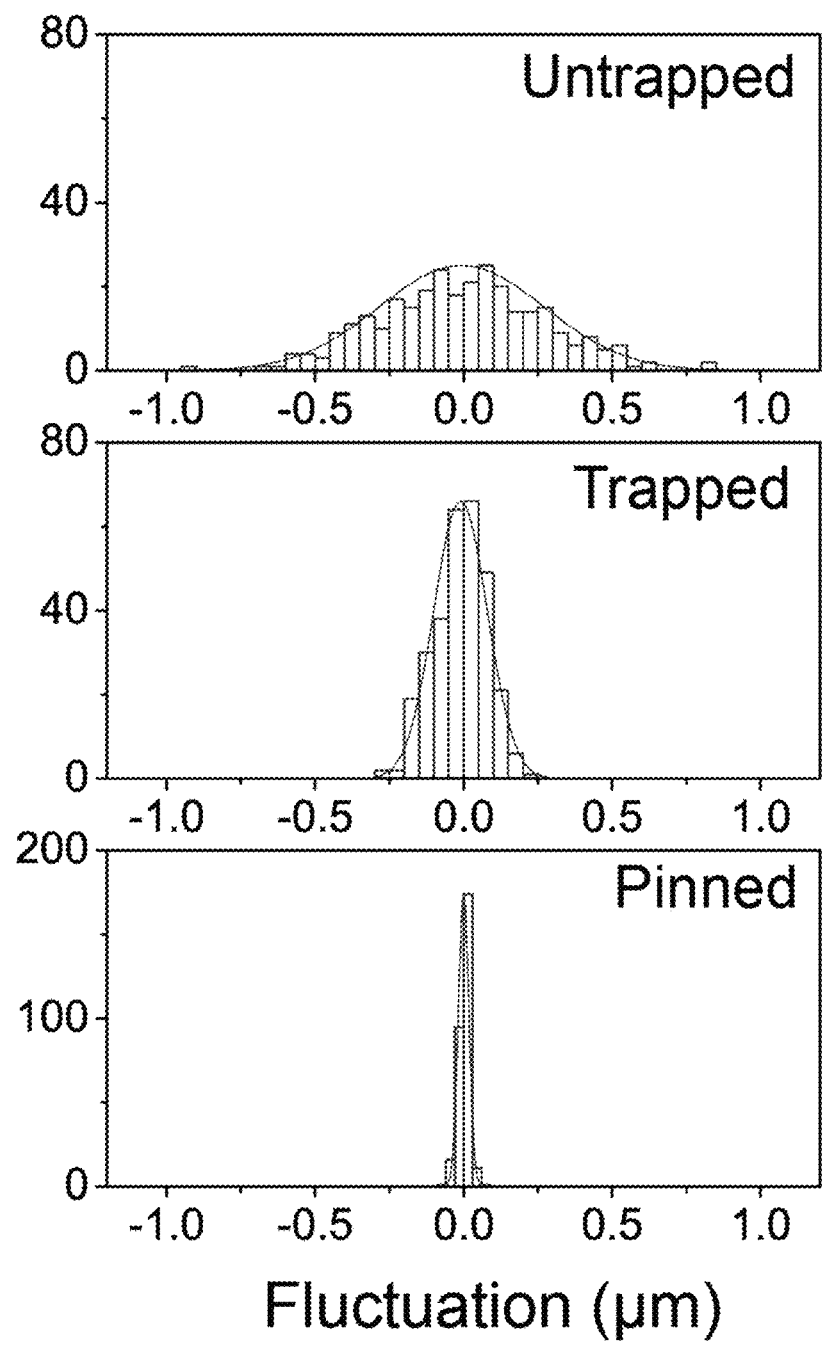
FIG. 9f shows a histogram of fluctuations for an untrapped bead, along with beads trapped on MAPT suspended in a fluid and on MAPT pinned to a substrate, in accordance with an embodiment of the present subject matter.

FIG. 9f demonstrate the various levels of localization achievable with the MAPTs. A histogram of position fluctuations of a 500 nm bead trapped on a pinned and an unpinned MAPT, along with an untrapped bead for comparison is plotted in the FIG. 9f. The fluctuations of the bead on the unpinned MAPT arises due to thermal fluctuations of the suspended helix, which in turn depends on the size of the MAPT. The bead on the pinned MAPT was strongly localized, as would be expected in a standard plasmonic tweezer.

Further, in an embodiment, the present subject matter relates to a method for manipulation of particles within the microfluid chamber and the relative advantages working with MAPT. The disclosures exemplify method of manufacture comprising: fabricating magnetically actuated nanostructures; integrating plasmonic elements with the magnetically actuated nanostructures to develop a Magnetically Augmented Plasmonic Tweezers (MAPT); and manipulating the particle in the fluid. In an aspect, the manipulation comprises: driving the MAPT towards a particle at a first location in the fluid medium by a driving mechanism; trapping the particle upon illumination using an optical source; transporting the trapped particle from the first location to a second location in the fluid medium at an actuation speed by the driving mechanism; and releasing the trapped particle at the second location upon reducing the illumination of the optical source below a threshold value. The trapping is due to electromagnetic near fields or thermoplasmonic effects. Further, as mentioned previously, the particles are dropped at the second location by reducing the illumination intensity of the source of light.

In an embodiment, multiple particles can be trapped, transported and released by single or multiple MAPTs at the same time. Further, the MAPTs can be used to selectively trap, transport, release and position a particle of particular size from a collection of particles. In addition, the MAPTs can be used to sort a collection of particles by choosing appropriate illumination intensity and/or speed of actuation. The MAPTs can also be used in conjunction with conventional optical tweezers.

Table 1 provided below shows the advantages of the MAPTs of the present subject matter over the conventional art.

TABLE 1

| Aspects of fluidic manipulation | Plasmonic tweezer | Micro-swimmer | MAPT (MAPT-D1 or MAPT-D2 or any other MAPT developed by integrating plasmonic tweezers with magnetic nanoswimmers) |
|---|---|---|---|
| Across large areas | No, Requires nano-patterned substrate | Yes | Yes |
| Manipulating sub-micron particles of any material | Yes | Yes | Yes |
| Speed of operation | Slow, diffusion dependent | Fast, externally controlled | Fast |
| Size selectivity | Largely preferred | Not demonstrated | Either larger or smaller |
| 3D manipulation | Mostly 2D | 3D | 3D |
| Summary | Efficient trapping at low optical power | Efficient at transport | Trap, transport and release of sub-micron particles in standard microfluidic chambers |

From the Table 1, it is clear that the individual strengths of two fluidic nano-manipulation techniques have been combined and integrated structurally in the MAPT, allowing optically (low power) controlled trap, transport, release and position of sub-micron particles across large areas at high speeds. The technology is scalable and does not require specialized nanopatterned surfaces implying easy integration in standard microfluidic applications.

Further, the MAPTs of the present subject matter can be used in environments that do not permit access, e.g., inside of a biological cell/tissue/organ, which can also include in vivo environments i.e. inside living systems. MAPTs can be fabricated on suitable designed plasmonic structures that would allow higher efficiency at the wavelength of interest. Furthermore, highly efficient MAPTs can be used under in vivo conditions, with illumination from outside or optical fiber inserted close to the region of interest. In an embodiment, the technique of the present subject matter may be integrated with other trapping techniques, e.g., those relying on chemical and magnetic methods. As previously discussed, method of actuation need not be limited to helical swimmers but can also work with swimming based on surface interactions (e.g. with rotated rods) and rotating fields, as well as gradient pulling (mentioned already). The MAPTs can be as large as the microfluidic device, and may also be actuated with non-magnetic means such electric fields, optical fields, sound etc.

Although embodiments for manipulation of particles within the fluid medium is described in language specific to structural features and/or methods, it is to be understood that the specific features and methods are disclosed as example embodiments for implementing the claimed subject matter.

We claim:

1. A method for trapping and maneuvering one or more colloidal particles inside a fluid, the method comprising:
    driving, by a magnetic field, one or more magnetically augmented tweezers towards the one or more colloidal particles, wherein each of the one or more magnetically augmented tweezers comprise a support structure, a magnetic component integrated in the support structure for motion control, and light absorbing nanostructures integrated in the support structure for optical trapping of particles;
    providing illumination by an optical source to activate the light absorbing nanostructures and trap the one or more colloidal particles;
    driving, by the magnetic field, the magnetically augmented tweezers with the trapped one or more colloidal particles to transport the one or more colloidal particles from a first location to a second location; and
    reducing the illumination of the optical source below a threshold value to release the one or more colloidal particles from the magnetically augmented tweezers at the second location.

2. The method as claimed in claim 1, wherein the magnetic field is a rotating magnetic field is provided by a triaxial Helmholtz coil to maneuver the one or more magnetically augmented tweezers.

3. The method as claimed in claim 1, further comprising, selectively trapping the one or more colloidal particles based on size, by tuning one of the illumination intensity of the optical source and frequency of the magnetic field driving the support structure.

4. The method as claimed in claim 1, further comprising tuning the illumination of the optical source to permanently trap chemically functionalized particles.

5. The method as claimed in claim 1, wherein the fluid is a biological fluid, wherein the biological fluid is selected from blood, mucus, cellular fluid, fluid in an organ, and fluid in a tissue, and wherein the biological fluid is inside a lab-on-chip device.

6. The method as claimed in claim 1, wherein the magnetic field is selected from gradient magnetic field, rotating magnetic field, oscillating magnetic field, and combination thereof.

7. The method as claimed in claim 1, wherein the method comprises binding the magnetically augmented tweezers onto a substrate using radiation pressure from an illumination.

8. The method as claimed in claim 1, wherein the method is to position cargoes in a microfluidic chamber.

9. The method as claimed in claim 1, wherein the method is for trapping and releasing biological material.

10. The method as claimed in claim 1, wherein trapping the particles by the light absorbing nanostructures is by one or more of thermophoretic force, near-field plasmonic force, convective force, plasmon-induced electric field, thermal effects, and combinations thereof.

11. The method as claimed in claim 1, wherein the support structure is one of beads, rods, and helical structures.

* * * * *